(12) United States Patent
Tang

(10) Patent No.: US 12,721,747 B2
(45) Date of Patent: Sep. 1, 2026

(54) HAND WARMER WITH BUILT-IN CABLE

(71) Applicant: Huixiang Tang, Hunan (CN)

(72) Inventor: Huixiang Tang, Hunan (CN)

( * ) Notice: Subject to any disclaimer, the term of this patent is extended or adjusted under 35 U.S.C. 154(b) by 0 days.

(21) Appl. No.: 19/333,343

(22) Filed: Sep. 19, 2025

(65) Prior Publication Data

US 2026/0000536 A1 Jan. 1, 2026

(51) Int. Cl.

| | |
|---|---|
| ***A41D 13/005*** | (2006.01) |
| ***A61F 7/00*** | (2006.01) |
| ***H02J 7/70*** | (2026.01) |

(52) U.S. Cl.

CPC ................ *A61F 7/007* (2013.01); *H02J 7/70* (2026.01); *A61F 2007/0036* (2013.01); *A61F 2007/0078* (2013.01)

(58) Field of Classification Search

CPC .............. A61F 7/007; A61F 2007/0036; A61F 2007/0078; H02J 7/0042

USPC ........................................................ 126/204

See application file for complete search history.

(56) References Cited

U.S. PATENT DOCUMENTS

| | | | | |
|---|---|---|---|---|
| 11,567,517 | B1 * | 1/2023 | Zhu | H02J 7/0063 |
| 2023/0422353 | A1 * | 12/2023 | Hu | H05K 5/0086 |

FOREIGN PATENT DOCUMENTS

| | | | |
|---|---|---|---|
| CN | 210330886 U | * | 4/2020 |
| CN | 211271578 U | * | 8/2020 |

OTHER PUBLICATIONS

CN 211271578, 2020.*
CN 210330886, 2019.*

* cited by examiner

*Primary Examiner* — Avinash A Savani

(74) *Attorney, Agent, or Firm* — Hawaii Patent Services; Nathaniel K. Fedde; Kenton N. Fedde

(57) ABSTRACT

The present disclosure relates to a hand warmer with a built-in cable, comprising: a housing; a data cable, one end of which is arranged within the housing; a charging plug, connected to the end of the data cable away from the housing; and a hand warming assembly, arranged on the housing and electrically connected to the data cable, for generating heat; wherein the hand warming assembly can receive external electrical energy for charging through the data cable and the charging plug, while also being capable of supplying power to external devices through the data cable and the charging plug.

17 Claims, 6 Drawing Sheets

HAND WARMER WITH BUILT-IN CABLE

TECHNICAL FIELD

The present disclosure relates to the technical field of hand warmers, particularly to a hand warmer with a built-in cable.

BACKGROUND

Traditional hand warmers have various technical issues: on one hand, they rely on external charging cables for power, which not only adds extra carrying burden and inconvenience but also risks affecting normal use due to lost cables. Additionally, during charging or powering other devices, users must locate and connect external charging cables, resulting in cumbersome operations and an inability to achieve fast charging or power supply, significantly reducing convenience. On the other hand, their functionality is relatively limited, offering only hand warming, while lacking dedicated portable hanging structures, making it difficult to conveniently store or secure during travel, further increasing carrying difficulty.

For example, U.S. Pat. No. 12,115,099B2 discloses a combined type hand warmer that uses snap-fit or magnetic detachable units, effectively addressing the limitation of single-hand warming and providing users with an efficient, multifunctional, and portable heating solution. However, it still relies on external charging cables during the charging process, which not only increases carrying burden and risks disruption due to lost cables but also requires repeated plugging and unplugging during charging or powering peripherals, leading to cumbersome operations and an inability to achieve fast charging or power supply, significantly reducing convenience. Moreover, the product lacks dedicated portable hanging structures, making it difficult to easily store or secure during travel, further limiting its practical convenience.

SUMMARY

The present disclosure provides a hand warmer with a built-in cable to solve the problems mentioned in the background art.

A hand warmer with a built-in cable comprises a housing; a data cable, with one end arranged within the housing; a charging plug connected to an end of the data cable away from the housing; and a hand warming assembly arranged on the housing and electrically connected to the data cable for generating heat. The hand warming assembly is capable of receiving external electrical energy for charging through the data cable and the charging plug, and the hand warming assembly is also capable of supplying power to external devices through the data cable and the charging plug.

A hand warmer with a built-in cable comprises a housing suitable for single-handed holding; a data cable, with one end arranged inside the housing; a charging plug connected to an end of the data cable away from the housing; a hand warming assembly arranged on the housing and electrically connected to the data cable for generating heat; and a placement slot formed on one side of the housing, with a shape thereof adapted to the charging plug, for storing the charging plug and making an outer surface of the charging plug substantially flush with a side wall of the housing. The hand warming assembly is capable of receiving external power for charging through the data cable and the charging plug, and the hand warming assembly is also capable of supplying power to external devices through the data cable and the charging plug.

To achieve the above object, the present disclosure adopts the following technical solutions:

By integrating the data cable in a fixed manner onto the housing, the problem of easily losing a separate data cable is effectively resolved. Through the cooperation of the data cable and the charging plug, bidirectional functionality is achieved—charging the hand warmer itself and supplying power to external devices—expanding the product's utility. The interaction between the placement slot and data cable forms a hangable loop structure, providing a convenient carrying method beyond handheld use, helping to reduce hand strain and enhance user experience.

BRIEF DESCRIPTION OF DRAWINGS

The drawings, which form part of this application, are included to provide further understanding of the present disclosure. The illustrative embodiments and the descriptions thereof serve to explain the present disclosure and do not constitute undue limitations. In the drawings.

REFERENCE SIGNS

Figure 1:
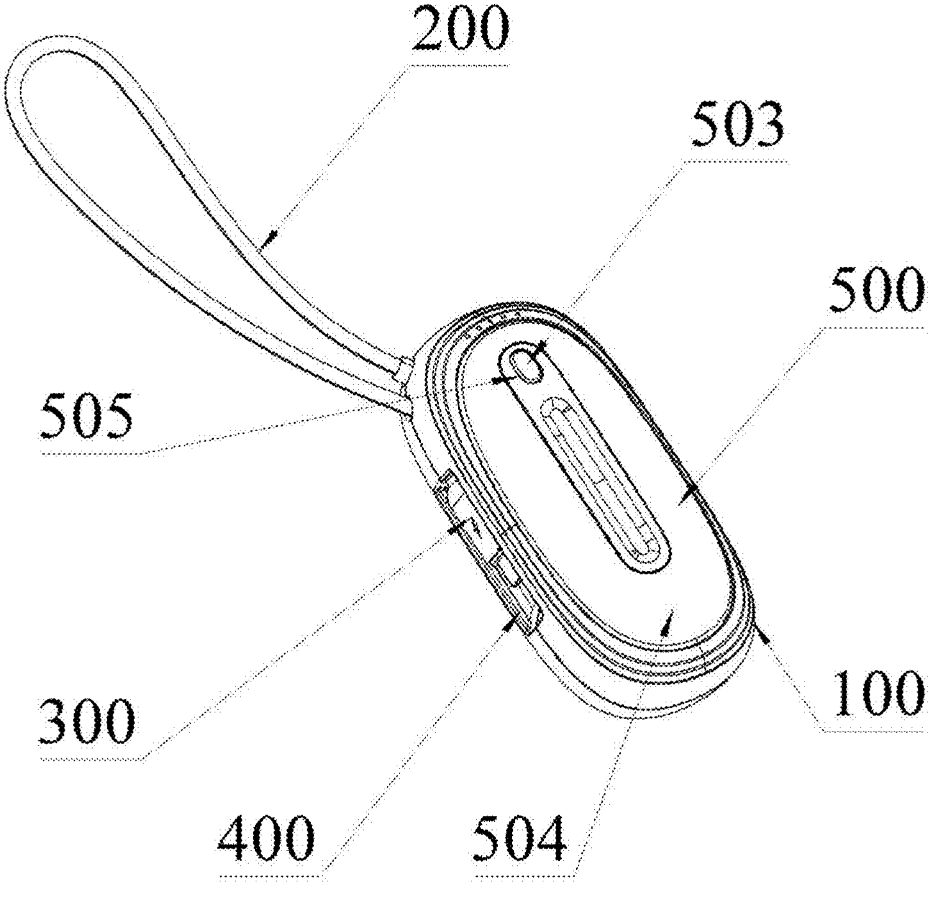
FIG. 1 is a perspective view of an embodiment provided by the present disclosure.

Housing (100); Data cable (200); Plug-in component (201); Socket (202); First through-hole (203); Second through-hole (204); Charging plug (300); Placement slot (400); Hand warming assembly (500); Battery (501); Mainboard (502); Button (503); Heating sheet (504); Mounting hole (505); Connecting plate (506); Connecting hole (507); Mounting slot (508).

DESCRIPTION OF EMBODIMENTS

The technical solution in the embodiment of the present disclosure will be clearly and completely described below with reference to the drawings. Obviously, the described embodiment is part of, rather than all of the embodiments of the present disclosure. The following description of at least one exemplary embodiment is illustrative in nature and is in no way intended to limit the present disclosure, its application or uses. Based on the embodiments in the present disclosure, all other embodiments obtained by those skilled in the art without creative work belong to the scope of protection of the present disclosure.

It should be noted that the terminology used here is only for describing specific embodiments, and is not intended to limit exemplary embodiments according to the present application. As used herein, the singular form is also intended to include the plural form unless the context clearly indicates otherwise. Furthermore, it should be appreciated that when the terms "comprising" and/or "including" are used in this specification, they specify the presence of features, steps, operations, devices, components and/or combinations thereof.

Unless otherwise specified, the relative arrangement of components and steps, numerical expressions and numerical values set forth in these embodiments do not limit the scope of the present disclosure. At the same time, it should be appreciated that for the convenience of description, the dimensions of various parts shown in the drawings are not drawn according to the actual scale relationship. Techniques, methods and equipment known to those skilled in the art may not be discussed in detail, but in appropriate cases, they should be regarded as part of the authorization specification. In all the examples shown and discussed herein, any specific values should be interpreted as illustrative, and not as limiting. Therefore, other examples of exemplary embodiments may have different values. It should be noted that similar numbers and letters indicate similar items in the following drawings, therefore once an item is defined in one drawing, it does not need to be further discussed in subsequent drawings.

Figure 2:
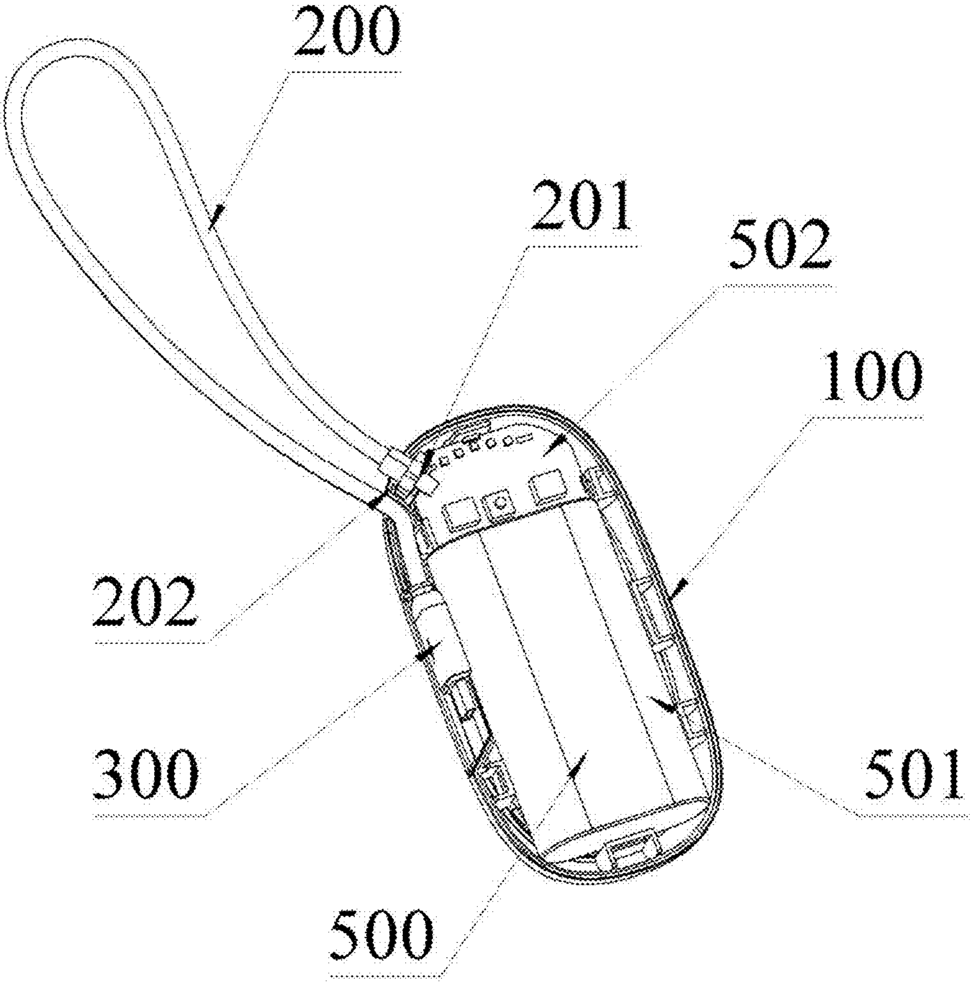
FIG. 2 is a schematic diagram of the internal structure of FIG. 1.

As shown in FIGS. 1 and 2, a hand warmer with a built-in cable includes a housing 100 and a data cable 200. The housing 100 is designed for single-handed holding. One end of the data cable 200 is located inside the housing 100, while the other end is equipped with a charging plug 300. A placement slot 400, adapted to the shape of the charging plug 300, is provided on one side of the housing 100 to securely store the charging plug 300, ensuring its outer surface is roughly flush with the sidewall of the housing 100. This maintains an aesthetically pleasing appearance while effectively preventing accidental detachment. The housing 100 also features a hand warming assembly 500, which is electrically connected to the data cable 200, providing hand-warming functionality. The charging plug 300 is one of the following: USB Type-A, USB Type-C, or Lightning. It connects to an external power source through the charging plug 300 to charge the hand warming assembly 500, or the hand warming assembly 500 can supply power to other devices through the data cable 200 and the charging plug 300.

Figure 3:
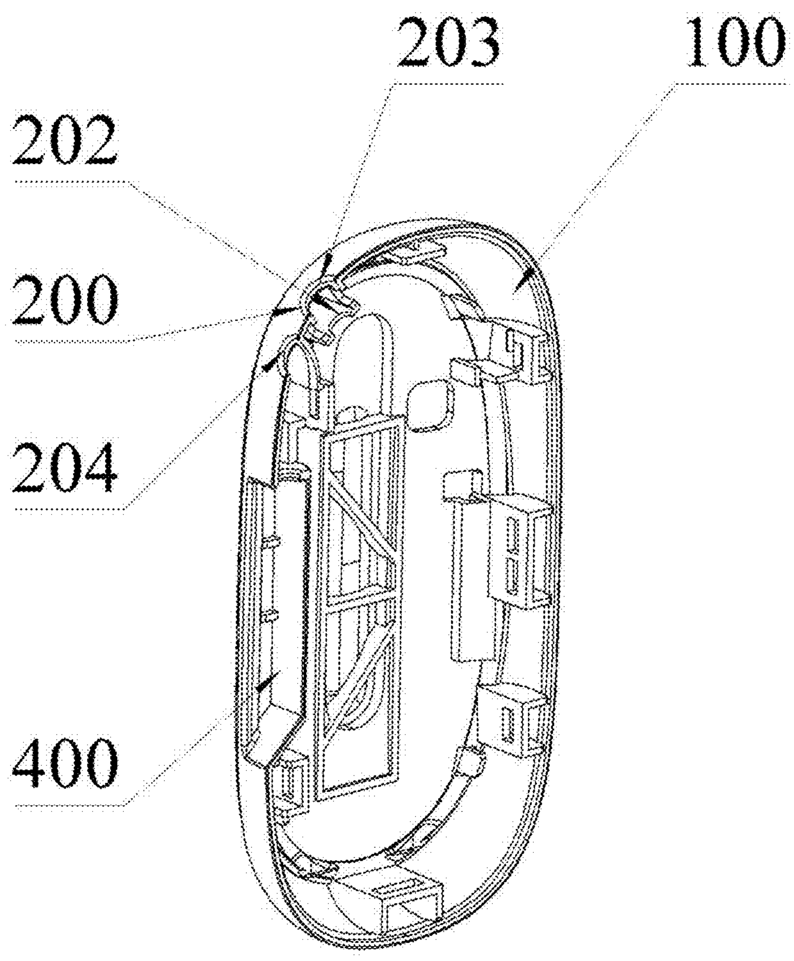
FIG. 3 is a schematic diagram of the socket, the first through-hole and the second through-hole in FIG. 2.
Figure 4:
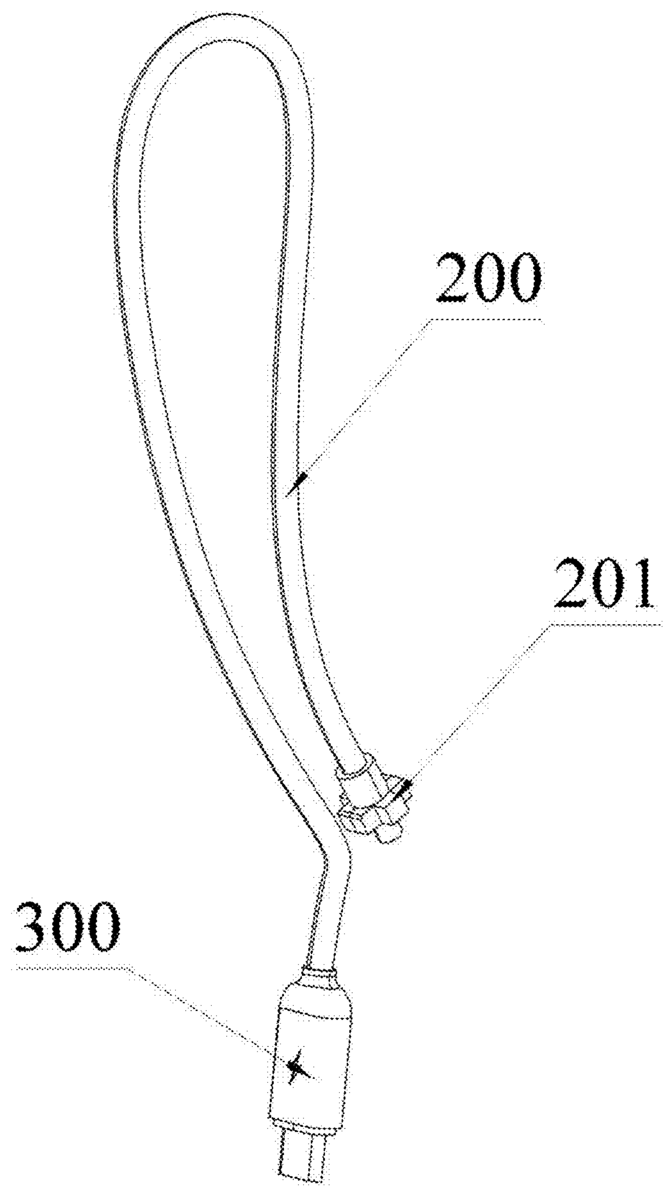
FIG. 4 is a schematic diagram of the data cable and the charging plug in FIG. 2.
Figure 5:
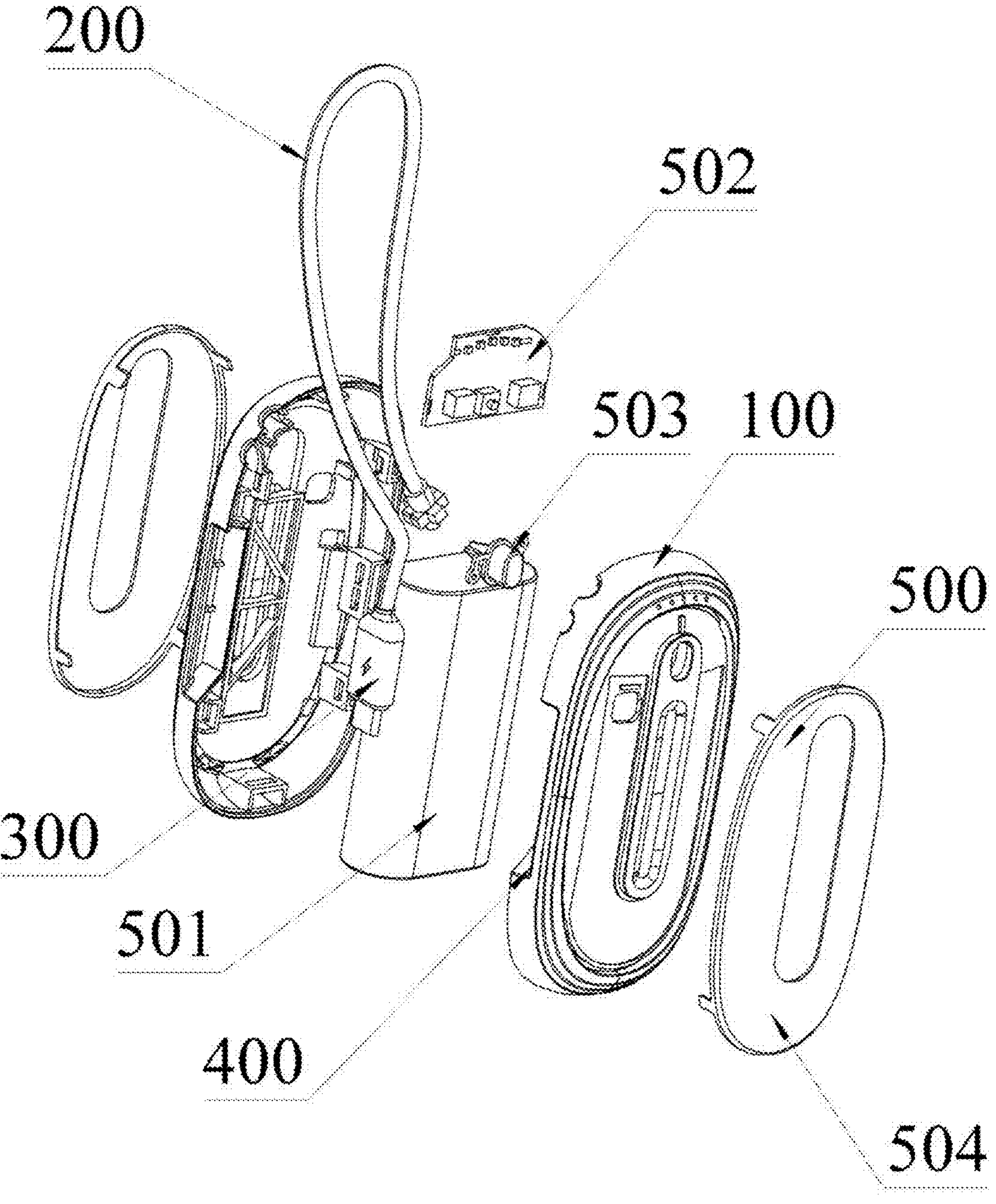
FIG. 5 is an exploded view of the hand warming assembly in FIG. 1.
Figure 6:
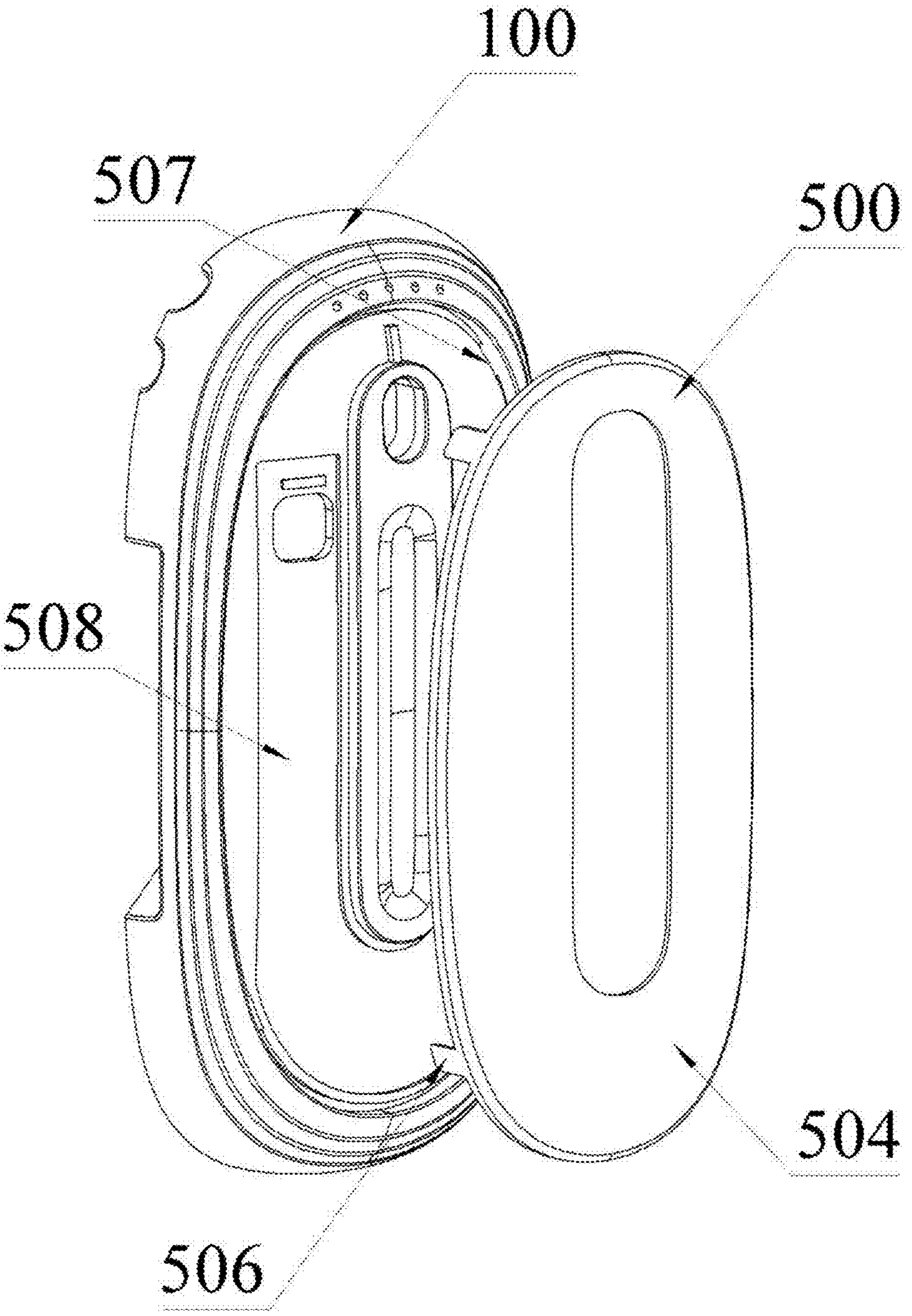
FIG. 6 is a schematic diagram of the connecting plate, connecting hole, and mounting slot in FIG. 5.

As shown in FIGS. 2 to 4, one end of the data cable 200 is equipped with a cross-shaped plug-in component 201. The interior of the housing 100 features a socket 202 designed to match the plug-in component 201. The plug-in component 201 is inserted into the socket 202, and their tight fit not only ensures reliable physical fixation, preventing the data cable 200 from being pulled out, but the cross-shaped structure also effectively prevents relative rotation of the plug-in component 201 within the socket 202, guaranteeing stable and durable electrical connectivity. The housing 100 is provided with a first through-hole 203 connected to the socket 202. The data cable 200 passes through the first through-hole 203 and extends outside the housing 100, facilitating the use of the data cable 200 while preventing its loss when not in use.

As shown in FIGS. 2 to 4, the housing 100 is provided with a second through-hole 204 connected to the placement slot 400. The data cable 200 passes through the second through-hole 204 and is connected to the charging plug 300. The diameter of the second through-hole 204 is slightly larger than that of the data cable 200, allowing sufficient sliding freedom for the data cable 200 while avoiding excessive looseness. By sliding the data cable 200 within the second through-hole 204, the charging plug 300 can be retrieved or its position adjusted, making it convenient to power other devices or charge the hand warming assembly 500 through an external power source. When the charging plug 300 is fully stored in the placement slot 400, the data cable 200 between the second through-hole 204 and the charging plug 300 naturally forms a ring-shaped part. Users can pass their wrist through this ring, allowing the entire hand warmer to hang from the wrist without needing to hold it constantly, significantly enhancing portability and comfort while effectively reducing hand fatigue during prolonged use.

As shown in FIGS. 1, 2, 5, and 6, the hand warming assembly 500 includes a battery 501 and a mainboard 502 housed inside the housing 100. The data cable 200 is connected to the mainboard 502, which is positioned above the battery 501. The battery 501 serves as the energy storage unit, while the mainboard 502, connected to the battery's positive and negative terminals through wires, manages the device's intelligent control functions, including charge/discharge management, temperature regulation, overheating protection, and short-circuit protection. The hand warming assembly 500 also includes a mounting hole 505 on the housing 100, inside which a button 503 is installed. The button 503 is connected to the switch on the mainboard 502, allowing users to power the device on/off and cycle through different heating levels (e.g., high and low) by pressing the button.

As shown in FIGS. 1, 2, 5, and 6, the hand warming assembly 500 also includes mounting slots 508 opened at both ends of the housing 100. The mounting slots 508 are equally spaced with multiple connecting holes 507, which are connected to the interior of the housing 100. A heating sheet 504 is snapped into the mounting slots 508, with both ends of the heating sheet 504 equipped with two connecting plates 506 that match the connecting holes 507. The connecting plates 506 are inserted into the connecting holes 507 and electrically connected to the mainboard 502 through wires. During assembly, the heating sheet 504 is aligned and pressed into the mounting slots 508, with its connecting plates 506 inserted into the connecting holes 507 on both sides. The connecting plates 506 are wired to the mainboard 502, establishing a stable electrical connection path from the mainboard 502 to the heating sheet 504. When the mainboard 502 operates, it supplies power to the heating sheet 504 through the connecting plates 506, causing the heating sheet 504 to generate heat and provide warmth for the hands. Upon receiving the startup command, the mainboard 502 directs the battery 501's power through the connecting plates 506 to the heating sheet 504, which quickly heats up to warm the user's hands.

In other embodiments (not shown), the housing 100 is equipped with a display screen, which is electrically connected to the mainboard 502 through wires. The display can show the battery 501's power level, the temperature of the heating sheet 504, and the heating level of the heating sheet 504, allowing users to easily monitor the hand warmer's status.

In other embodiments (not shown), the mating structure of the plug-in component 201 and the socket 202 can be redesigned into a rectangular shape. The socket 202 may be internally embedded with gold-plated spring pins, while the end face of the plug-in component 201 is equipped with gold-plated contacts corresponding to the spring pins. When the plug-in component 201 is inserted into the socket 202, electrical connection is achieved through the compression contact of the spring pins. This design facilitates the replacement of the data cable 200.

In other embodiments (not shown), the heating sheet 504 can be replaced with a flexible thick-film heating sheet. This heating sheet is directly adhered to the inner wall of the housing 100 using high-temperature-resistant pressure-sensitive adhesive. Its electrodes are soldered directly to the mainboard 502 through a flexible circuit board, eliminating the need for separate connecting plates 506 and connecting holes 507.

In other embodiments (not shown), the control interface is not limited to the button 503. A touch-sensing IC and capacitive touch pad can be installed in the mounting hole 505 to enable touch switching and slider-based temperature adjustment. Furthermore, a Bluetooth module can be integrated into the mainboard 502, allowing advanced functions such as wireless control of switching, temperature adjustment, and power level monitoring through a mobile app.

In other embodiments (not shown), the data cable 200 and the housing 100 can be fixedly connected using an inseparable, integrated injection-molding method to further enhance connection reliability.

In other embodiments (not shown), the notch of the placement slot 400 can be equipped with an elastic cover featuring a snap-fit mechanism. Once the charging plug 300 is inserted, closing the cover can further prevent it from falling or being lost.

In other embodiments (not shown), one end of the data cable 200 is located inside the housing 100, while the other end is fitted with a dual-purpose USB Type-C/Lightning charging plug 300. The sidewall of the housing 100 is provided with a magnetic placement slot 400 (embedded with neodymium magnets; the charging plug 300 and corresponding area of the housing 100 are equipped with iron plates for secure storage and easy access), ensuring the outer surface of the charging plug 300 aligns flush with the sidewall when stored. One end of the data cable 200 features a circular magnetic plug-in component (with an embedded ring-shaped magnet), while the housing 100 internally includes a magnetic socket with alignment pins (the socket base contains matching magnets, and the pins insert into the central positioning hole of the plug-in component). The plug-in component and socket are secured through magnetic attraction and pin alignment, preventing both detachment and rotational movement. The housing 100 has a first through-hole 203 (0.5 mm larger in diameter than the data cable 200 for flexibility) connected to the socket. Inside the housing 100, a polymer lithium battery 501 and mainboard 502 (integrated with charge/discharge management chip BQ25703) are connected through wiring. The exterior of the housing 100 features a recess where a flexible graphene heating film is adhered with thermal conductive glue; its conductive contacts are electrically linked to the mainboard 502 through spring plates. The top of the housing 100 includes a mounting hole for an embedded OLED temperature display, connected to the mainboard 502 for real-time temperature readings. Adjacent to the display is a silicone button (linked to the mainboard switch) for power on/off and three-level temperature adjustment (40° C., 45° C., 50° C.). The bottom of the housing 100 has a second through-hole 204 connected to the placement slot 400, allowing the data cable 200 to form an adjustable-length segment when threaded through, with a maximum extension of 1.2 m. When retracted, the ring-shaped part can be hung around the wrist.

In other embodiments (not shown), it includes a foldable housing (composed of a left shell and a right shell connected by a damping hinge, with a folding angle of 0-180°, reducing the volume by 40% when folded) and a built-in automatic retractable data cable 200. The retractor is fixed inside the left shell (including a spool, a coil spring, and a ratchet stop mechanism; the spring force enables automatic retraction of the data cable 200, while the ratchet mechanism prevents reverse rotation during retraction). One end of the data cable 200 is connected to a conductive slip ring inside the retractor (ensuring uninterrupted electrical connection during rotation), and the other end is equipped with a USB Type-A charging plug 300. The side wall of the right shell features a stepped placement slot 400 (adapted to the stepped structure of the charging plug 300, ensuring no protrusion when stored). The left shell has a retraction opening (2 mm narrower than the charging plug 300 to prevent it from entering the shell during retraction), and the data cable 200 extends from this opening. Inside the left shell are a battery 501 and a mainboard 502 (integrated with an overheating protection module that automatically cuts off power when the temperature is ≥55° C.). The right shell has symmetrically installed cavities, where PTC heating sheets are secured through clips and connected to the mainboard 502 through wires passing through threading holes in the hinge. The outer surface of the right shell features raised rubber buttons (linked to the mainboard switch, with a pressing stroke 2 mm), while the left shell has a Type-C charging port (allowing direct charging through an external data cable 200 as a backup charging method). When the housing 100 is folded, the left and right shells are secured by magnetic clasps (with an adsorption force≥3N), facilitating storage and portability; when unfolded, it conforms to both sides of the hand for simultaneous heating. When connected to an external power source through the charging plug 300, the mainboard 502 controls battery 501 charging and automatically cuts off power when fully charged. After pressing the button 503 to power on, the mainboard 502 regulates current input to the heating film based on the selected level, ensuring even heat distribution and heat conduction through the curved housing, with the temperature displayed on the screen. When stored, the charging plug 300 is magnetically attached to the placement slot 400, and the data cable 200 naturally forms a hanging loop.

In summary, the present disclosure achieves the following technical effects:

By integrating the data cable 200 into the housing 100 in a fixed manner (e.g., through the plug-in component 201 and socket 202), the issue of easily losing a separate data cable 200 is effectively resolved. The combination of the data cable 200 and charging plug 300 enables dual functionality—charging the hand warmer itself and external devices, expanding product utility. The interaction between the placement slot 400 and data cable 200 forms a hanging loop structure, providing a convenient carrying method beyond handheld use, reducing hand strain, and enhancing user experience.

In the description of the present disclosure, it should be appreciated that directional terms such as "front, rear, up, down, left, right", "horizontal, vertical, perpendicular, horizontal" and "top, bottom" etc. indicate the orientation or positional relationship based on the orientation or positional relationship shown in the drawings, and are only for the convenience of describing the present disclosure and simplifying the description. In the absence of a contrary explanation, these directional terms do not indicate or imply that the device or element referred to must have a specific orientation or be constructed and operated in a specific orientation, and therefore should not be understood as limiting the scope of protection of the present disclosure; the directional terms "inside, outside" refer to the inside and outside relative to the contour of each component itself.

For the convenience of description, spatial relative terms such as "on . . . ", "above . . . ", "on the upper surface of . . . ", "upper" etc. may be used here to describe the spatial positional relationship of a device or feature with other devices or features as shown in the drawings. It should be appreciated that spatial relative terms are intended to encompass different orientations of the device in use or operation other than the orientation described in the drawings. For example, if the device in the drawing is inverted, the device described as "above other devices or structures" or "on other devices or structures" will subsequently be positioned as "below other devices or structures" or "under other devices or structures". Thus, the exemplary term "above" can include both "above" and "below" orientations. The device can also be positioned in other different ways (rotated 90 degrees or in other orientations), and the spatial relative descriptions used here should be interpreted accordingly.

In addition, it should be noted that the use of terms such as "first", "second" etc. to define components is for the convenience of distinguishing the corresponding components. Unless otherwise stated, the above terms have no special meaning, and therefore should not be understood as limiting the scope of protection of the present disclosure.

The above description is only a preferred embodiment of the present disclosure and is not intended to limit the present disclosure. For those skilled in the art, the present disclosure can have various modifications and changes. Any modifications, equivalent replacements, improvements etc. made within the spirit and principles of the present disclosure should be included within the scope of protection of the present disclosure.

What is claimed is:

1. A hand warmer with a built-in cable, comprising:

a housing; and a data cable, with one end arranged within the housing; and a charging plug connected to an end of the data cable away from the housing, and a placement slot for accommodating the charging plug is provided on one side of the housing;

wherein the housing is provided with a second through-hole connected to the placement slot, and the data cable passes through the second through-hole to be connected with the charging plug;

when the charging plug is stored in the placement slot, a portion of the data cable between the second through-hole and the charging plug forms a ring-shaped part usable for hanging; and a hand warming assembly arranged on the housing and electrically connected to the data cable for generating heat;

wherein the hand warming assembly is capable of receiving external electrical energy for charging through the data cable and the charging plug, and the hand warming assembly is also capable of supplying power to external devices through the data cable and the charging plug.

2. The hand warmer with the built-in cable according to claim 1, wherein the data cable is detachably connected to the housing.

3. The hand warmer with the built-in cable according to claim 2, wherein an end of the data cable adjacent to the housing is provided with a plug-in component, a socket adapted to the plug-in component is arranged within the housing, and the plug-in component is inserted into the socket for fixation.

4. A hand warmer with a built-in cable, comprising:

a housing; and a data cable, with one end arranged within the housing, wherein the data cable is detachably connected to the housing; and a charging plug connected to an end of the data cable away from the housing, and a placement slot for accommodating the charging plug is provided on one side of the housing; and a hand warming assembly arranged on the housing and electrically connected to the data cable for generating heat;

wherein the hand warming assembly is capable of receiving external electrical energy for charging through the data cable and the charging plug, and the hand warming assembly is also capable of supplying power to external devices through the data cable and the charging plug wherein an end of the data cable adjacent to the housing is provided with a plug-in component, a socket adapted to the plug-in component is arranged within the housing, and the plug-in component is inserted into the socket for fixation, wherein the plug-in component is cross-shaped, and the socket is a cross-shaped slot adapted to the plug-in component, to prevent relative rotation of the plug-in component within the socket.

5. The hand warmer with the built-in cable according to claim 1, wherein the hand warming assembly comprises a battery, a mainboard and a heating sheet; and the mainboard is electrically connected to the battery, the data cable and the heating sheet respectively, for controlling charging, discharging, and heating processes.

6. The hand warmer with the built-in cable according to claim 5, wherein a button is provided on a surface of the housing, connected to a switch on the mainboard, for controlling turning, turning off or function switching of the hand warmer.

7. The hand warmer with the built-in cable according to claim 6, wherein different heating levels can be cyclically switched through the button.

8. The hand warmer with the built-in cable according to claim 5, wherein the heating sheet is detachably arranged on the housing.

9. The hand warmer with the built-in cable according to claim 8, wherein the housing is provided with a mounting slot, and connecting holes are formed in the mounting slot; and both ends of the heating sheet are provided with connecting plates adapted to the connecting holes, the connecting plates are inserted into the connecting holes and electrically connected to the mainboard, thereby achieving fixation and electrical connection of the heating sheet.

10. The hand warmer with the built-in cable according to claim 1, wherein the charging plug is one of a USB Type-A, USB Type-C, or Lightning interface.

11. A hand warmer with a built-in cable, comprising:

a housing suitable for single-handed holding; and a data cable, with one end arranged inside the housing; and a charging plug connected to an end of the data cable away from the housing; and a hand warming assembly arranged on the housing and electrically connected to the data cable for generating heat; and a placement slot formed on one side of the housing, with a shape thereof adapted to the charging plug, for storing the charging plug and making an outer surface of the charging plug substantially flush with a side wall of the housing, wherein the housing is provided with a second through-hole connected to the placement slot, and the data cable passes through the second through-hole and is connected to the charging plug wherein when the charging plug is stored in the placement slot, the data cable between the second through-hole and the charging plug forms a circular hanging part;

wherein the hand warming assembly is capable of receiving external power for charging through the data cable and the charging plug, and the hand warming assembly is also capable of supplying power to external devices through the data cable and the charging plug.

12. The hand warmer with the built-in cable according to claim 11, wherein an end of the data cable inside the housing is provided with a plug-in component, a socket adapted to the plug-in component is arranged inside the housing, and the plug-in component is inserted into the socket.

13. The hand warmer with the built-in cable according to claim 11, wherein the hand warming assembly comprises a battery, a mainboard and a heating sheet, and the mainboard is electrically connected to the battery, the data cable and the heating sheet respectively.

14. The hand warmer with the built-in cable according to claim 13, wherein the housing is provided with a button connected to a switch on the mainboard for controlling turning on and turning off of the hand warmer and adjusting heating levels.

15. The hand warmer with the built-in cable according to claim 14, wherein mounting slots are formed at both ends of the housing, and the heating sheet is snapped into the mounting slots.

16. The hand warmer with the built-in cable according to claim 15, wherein both ends of the heating sheet are provided with connecting plates, the mounting slots are provided with connecting holes adapted to the connecting plates, and the connecting plates are inserted into the connecting holes and electrically connected to the mainboard.

17. The hand warmer with the built-in cable according to claim 12, wherein the housing is provided with a first through-hole connected to the socket, and the data cable passes through the first through-hole to extend out of the housing.

* * * * *